United States Patent [19]

Pasternak et al.

[11] Patent Number: 5,182,022
[45] Date of Patent: Jan. 26, 1993

[54] DEWATERING OF CONCENTRATED AQUEOUS SOLUTIONS BY PERVAPORATION

[75] Inventors: Mordechai Pasternak, Spring Valley; John Reale, Jr., Wappingers Falls, both of N.Y.

[73] Assignee: Texaco Inc., White Plains, N.Y.

[21] Appl. No.: 717,764

[22] Filed: Jun. 19, 1991

Related U.S. Application Data

[63] Continuation of Ser. No. 146,763, Jan. 22, 1988, abandoned.

[51] Int. Cl.$^5$ .................... B01D 13/00; C07C 29/76; C07C 31/18
[52] U.S. Cl. .................... 210/638; 210/640; 210/500.27; 210/500.36; 159/DIG. 27; 203/18; 568/868
[58] Field of Search ............ 203/14, 18, 89, 99, 203/39, 40; 210/640, 638, 500.27, 500.36; 159/DIG. 27, DIG. 28; 568/868

[56] References Cited

U.S. PATENT DOCUMENTS

| | | | |
|---|---|---|---|
| 3,750,735 | 8/1973 | Chiang et al. | 210/640 |
| 4,067,805 | 1/1978 | Chiang et al. | 210/654 |
| 4,526,948 | 7/1985 | Resnick | 526/247 |
| 4,690,766 | 9/1987 | Linder et al. | 210/500.42 |
| 4,728,429 | 3/1988 | Cabasso et al. | 210/640 |

FOREIGN PATENT DOCUMENTS 2103536  2/1983  United Kingdom ............... 568/916

Primary Examiner—Wilbur Bascomb, Jr.
Attorney, Agent, or Firm—Robert A. Kulason; James J. O'Loughlin; Carl G. Seutter

[57] ABSTRACT

Charge aqueous solution containing 85 w % ethylene glycol is concentrated by pervaporation across a sulfonated polyethylene membrane to yield retentate containing 95 w % ethylene glycol.

1 Claim, No Drawings

DEWATERING OF CONCENTRATED AQUEOUS SOLUTIONS BY PERVAPORATION

This is a continuation of application Ser. No. 07/146,763, filed Jan. 22, 1988 and now abandoned.

FIELD OF THE INVENTION

This invention relates to the dewatering of concentrated aqueous solutions. More particularly it relates to a process for treating concentrated aqueous solutions to yield product characterized by decreased content of water.

BACKGROUND OF THE INVENTION

As is well known to those skilled in the art, it is possible to remove water from mixtures thereof with organic liquids by various techniques including adsorption or distillation. These conventional processes, particularly distillation, are however characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, could require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the vapor pressure of the permeating species.

Illustrative membranes which have been employed in prior art techniques include those set forth in the following table:

TABLE

| Separating Layer | References |
| --- | --- |
| - Nafion brand of perfluorosulfonic acid | - Cabasso and Liu J. Memb. Sci. 24, 101 (1985) |
| - Sulfonated polyethylene | - Cabasso, Korngold & Liu J. Pol. Sci: Letters, 23, 57 (1985) |
| - Fluorinated Polyether or Carboxylic Acid fluorides | - U.S. Pat. No. 4,526,948 to Dupont as assignee of Resnickto |
| - Selemion AMV blend of Asahi Glass cross-linked styrene butadiene (with quaternary ammonium residues on a polyvinyl chloride backing | - Wentzlaff Boddeker & Hattanbach J. Memb. Sci. 22, 333 (1985) |
| - Cellulose triacetate | - Wentzlaff, Boddeker & Hattanback J. Memb. Sci. 22, 333 (1985) |
| Polyacrylontrile | - Neel, Aptel, & Clement Desalination 53, 297 (1985) |
| - Crosslinked Polyvinyl Alcohol | - Eur. Patent 0 096 339 to GFT as assignee of Bruschke |

The cost effectiveness of a membrane is determined by the selectivity and productivity. Of the membranes commercially available, an illustrative membrane of high performance is that disclosed in European patent 0 096 339 A2 of GFT as assignee of Bruschke - published Dec. 21, 1983.

European Patent 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

It is an object of this invention to provide a process for dewatering concentrated aqueous solutions. Other objects will be apparent to those skilled in the art.

STATEMENT OF THE INVENTION

In accordance with certain of its aspects, this invention is directed to a method which comprises passing a charge aqueous concentrated solution of an organic oxygen-containing component which is substantially miscible with water into contact with, as a pervaporation membrane, a high molecular weight resin in membrane form, bearing a pendant acid group which membrane has been contacted with a counter ion of metals of Groups I A, I B, IVB, VB or VI B or VIII of the Periodic Table or $R_4N^+$ wherein at R is a hydrocarbyl group containing less than six carbon atoms and the sum of all the carbon atoms in the R groups is at least 4 and less than 20;

maintaining a pressure drop across said pervaporation membrane thereby forming a retentate containing increased content of organic oxygen-containing component and decreased content of water and a permeate containing decreased content of organic oxygen-containing component and increased content of water; and recovering said permeate containing decreased content of organic oxygen-containing component and increased content of water.

DESCRIPTION OF THE INVENTION

The Charge Solution

The charge aqueous solution of organic oxygen-containing component which may be treated by the process of this invention may include oxygen-containing compounds such as alcohols, glycols, polyols, aldehydes, ketones, etc. When the oxygen-containing component is an alcohol, it may be for example ethanol, propanol, isopropanol, n-butanol, isobutanol, t-butanol, hexanols, octanols, etc. When the oxygen-containing component is a glycol it may be for example ethylene glycol, propylene glycol, butylene glycol, etc. When the oxygen-containing component is an aldehyde, it may for example be formaldehyde, acetaldehyde, etc. When the oxygen-containing component is a ketone, it may for example be acetone, methyl ethyl ketone, acetophenone, etc.

It is a particular feature of the process of this invention that the advantages thereof may be most readily apparent when the charge aqueous solution is a concentrated aqueous solution.

Although the advantages may be attained when the charge concentrated solution contains say 70 w % or more of organic oxygen-containing component, e.g., 70 w %–90 w %, it may be found that desired results may be obtained when the charge concentrated solutions are at or above the 80 w % level.

The instant process may find particular use in connection with other concentration techniques. For example, a particular charge solution may be concentrated by distillation up to a point at which further concentration by distillation may be uneconomical followed by further concentration using the process of this invention. A charge may, for example, be concentrated by distillation to a point at which an azeotrope is formed as in the case of ethanol-water followed by further concentration using the process of this invention. In alternative aspects, the process of the instant invention may be employed first, followed, for example, by distillation. Clearly in each case the number of separation steps and the particular sequence will depend on the economics of the particular system which of course depend on the composition and properties of the charge solution.

The process of this invention is found to be particularly useful in treating charge solutions containing 80-99+w %. ethylene glycol to recover product containing decreased quantities of water.

Illustrative charge solutions which may be employed in practice of the process of this invention may include:

| (i)   | 85 w % ethylene glycol |
|       | 15 w % water |
| (ii)  | 95 w % ethylene glycol |
| (iii) | 95 w % ethanol |
|       | 5 w % water |
| (iv)  | 80 w % acetaldehyde |
|       | 20 w % water |

THE MEMBRANE

The pervaporation membrane which may be utilized in practice of the process of this invention may be a high molecular weight resin in membrane form. The membrane may be formed of a non-porous material such as polyolefin (e.g. polyethylene, polypropylene, polystyrene, copolymers of ethylene-propylene, terpolymers of ethylene-propylene-third monomer such as 1,4-hexadiene or dichlopentadiene or ethylidene norbornene); vinyls such as polyvinyl chloride, polyvinyl acetate, etc., perfluorinated polyolefins, perfluorinated ether polymers, etc. Clearly the molecular weight of the membrane may vary depending on the species. The thickness of the membrane may typically be 80-190 microns.

The resins which may be employed in membrane form are characterized by the presence of a pendant acid group such as a —COOH group or more preferably a —SO$_3$H group. These may be introduced into the resin in known manner (if not already present therein) by functionalization with appropriate reagents.

A preferred class of membranes may include those which are perfluorinated hydrocarbons or ethers (i.e. contain substantially no hydrogen atoms other than those on the pendant acid e.g.—SO$_3$H groups). These membranes may preferably be characterized by the following formula

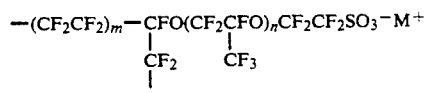

One acid resin membrane which is particularly preferred is that first set forth in the following table which lists illustration commercially available ion exchange membranes which may be employed:

TABLE

A. The Nafion-H 117 brand of perfluorinated resin membrane made by DuPont of a thickness of 190 microns, and having a formula

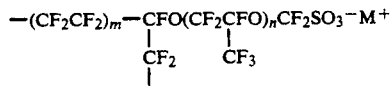

B. Sulfonated polyethylene

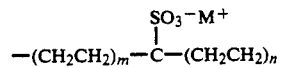

TREATMENT OF MEMBRANE

Treatment of the high molecular weight resin in membrane form bearing a pendant acid group to permit effective use in the process of this invention may include contacting the membrane with counter ions which may be derived from (i) a metal of Group I A (hydrogen or the alkali metals e.g. Na, K, Li, Rb, Cs or (ii) a metal of Group IB (Cu or Ag) or (iii) a transition metal such as one from Group IVB (Ti, Zr, Hf) or from Group VB (V, Nb, or Ta) or from Group VI B (Cr, Mo,W) or Group VIII (Fe, Co, Ni, Ru, Rh, Pd, Os, Ir, Pt) or (iv) a quaternary ammonium salt R$_4$NX wherein R is a hydrocarbon moiety having less than six carbon atoms and the sum of all the carbon atoms in the R groups is at least 4 and less than 20 and X is a halide, more preferably bromide. Treating to provide the counter ion may be carried out as by contacting at least the surface which is to contact the charge solution with a solution of agent containing the counter ion.

The treating agent to provide the counter ion may typically be an aqueous solution of a salt of the metal—a halide, sulfate, etc. When the counter ion is a metal, it is preferably an alkali metal (more preferably K, Li, Na or Rb) or a transition metal (preferably Cr$^{+3}$) and typically the treating agent may be in the form of an aqueous solution of e.g. lithium chloride, etc.

When the treating agent is a quaternary ammonium halide, it may be characterized by the formula R$_4$NX.

In the above formula, R may be an alkyl hydrocarbon group including such radicals when inertly substituted. When R is alkyl, it may be typically be methyl, ethyl, n-propyl, iso-propyl, n-butyl, i-butyl, or sec-butyl. R may be inertly substituted i.e. it may bear a non-reactive substituent such as alkyl, ether, halogen, etc. Typically inertly substituted R groups may include 3-chloropropyl, 2-ethoxyethyl, carboethoxymethyl, etc. The preferred R groups may be n-butyl.

The R groups may be different, although preferably they will be the same. X is preferably a halide, preferably chloride or bromide—most preferably bromide. Typical quaternary ammonium halides which may be employed (the first listed being preferred) may include:

TABLE tetramethyl ammonium bromide
tetraethyl ammonium bromide
tetra-n-propyl ammonium bromide
tetra-i-propyl ammonium bromide
tetra-n-butyl ammonium bromide
tetra-i-butyl ammonium bromide
tetraethyl ammonium chloride
tetramethyl ammonium iodide
tetrabutyl ammonium fluoride
methyl, tri-n-butyl ammonium bromide
ethyl, tri-n-propyl ammonium bromide
dimethyl, di-n-butyl bromide
trimethyl, butyl ammonium bromide etc.

The quaternary ammonium salt is characterized by the following criteria:

(i) the sum of the carbon atoms in all the R groups is at least 4 and less than 20.

(ii) each R group contains less than six carbon atoms.

When the treating agent is the quaternary ammonium salt, it may be employed as a solution in water or alcohol, typically 5 w %–50 w %, say 10 w % solution (corresponding to about 0.2M) in solvent, typically an alcohol such as isopropyl alcohol. Contact may be at 25° C. for 12–48 hours, say 24 hours with mild agitation. Thereafter, the treated membrane may be washed 2–5, say 3 times for 10–50 minutes, say 30 minutes at 20° C.–40° C., say 25° C. with isopropanol followed by washes with a 50/50 mixture of isopropanol and water and drying at 20° C.–40° C., say 25° C. for 5–20 minutes, say 10 minutes.

The membranes of this invention may be utilized in various configurations. It is, for example, possible to utilize the membrane in a plate-and-frame configuration in which the separating membrane layer may be mounted on a porous support layer.

In one preferred embodiment, it is possible to utilize the system of this invention as a tubular or hollow fibre. In this embodiment, the resin membrane may be extruded as a fine tube with a wall thickness of typically 0.001–0.1 mm. The extruded tubes may be passed through a bath of quaternary ammonium salt in solvent. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating membrane and permeate is collected in the shell side.

PERVAPORATION

It is a feature of this invention that it is found to be particularly effective when used in a pervaporation process. In pervaporation, a charge liquid containing a more permeable and a less permeable component is maintained in contact with a non-porous separating layer; and a pressure drop is maintained across that layer. A portion of the charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 1–10 mm. Hg.

For general background on pervaporation, note U.S. Pat. Nos. 4,277,344, 4,039,440; 3,926,798; 3,950,247; 4,035,291; etc.

It is a feature of this invention that the novel membrane may be particularly useful in pervaporation processes for dewatering aqueous solutions of organic oxygen-containing components typified by ethylene glycol. A typical charge may be a 80–95+w %, say 85 w %, aqueous solution of ethylene glycol.

In practice of the pervaporation process of this invention, the charge aqueous solution at 25° C.–120° C., say 80° C. may be passed into contact with the non-porous membrane of this invention. A pressure drop of about one atmosphere is commonly maintained across the membrane. Typically, the feed or charge side of the membrane is at about atmospheric pressure and the permeate or discharge side of the membrane is at a pressure of about 0.5–50 preferably 0.5–20, say 10 mm.Hg.

The permeate which passes through the membrane includes water and a small portion of oxygen-containing component from the charge liquid. Typically, the retentate contains 90–99.9, say 99 w % oxygenated compound. Permeate is condensed and recovered in liquid phase.

Pervaporation may typically be carried out at a flux of 0.01–10, say 0.50 gallons per square foot per day which corresponds to about 0.017–16.9, say 0.68 kilograms per square meter per hour (kmh). Typically, the units may have a selectivity (measured in terms of w% oxygen-containing component in the permeate during pervaporation at 25°–70° C.) of up to about 60%.

The Separation Factor S or Sep which represents the ability of the membrane to recover desired oxygenate is calculated as follows:

$$S = \frac{\left(\frac{X_n}{X_{mp}}\right)}{\left(\frac{X_n}{X_{mf}}\right)}$$

wherein $X_n$ and $X_m$ are the weight fractions of oxygen-containing component and water respectively in the permeate (P) and the feed (F). A system showing no separation at all would have a Separation Factor of 1; and a system showing perfect 100% separation would have a Separation Factor of infinity. The process of the instant invention may commonly have a separation factor of 5–600, typically 30–50, say about 45.

It will be apparent to those skilled in the art that the degree of concentration of oxygen-containing component in the permeate may be a function of several variables. Among these may be the composition of the membrane counter ion, the temperature and pressure of pervaporation, and the effective time of contact between the charge solution and the membrane or, alternatively expressed, the area of contact with the membrane.

For example it may be desirable in one embodiment to effect only a small increase in concentration of a soluble component or alternatively it may be desirable to augment the concentration substantially.

DESCRIPTION OF SPECIFIC EMBODIMENT

Practice of the process of this invention will be apparent to those skilled in the art from the following wherein, as elsewhere in this specification, all parts are parts by weight unless otherwise specified.

EXAMPLE I

In this example which represents the best mode of carrying out the process of this invention according to certain of its aspects, the charge solution is an 85 w % solution of ethylene glycol in water.

The membrane employed is sulfonated polyethylene (SPE) bearing pendant —$SO_3H$ groups. The membrane (without support layer or carrier layer) is mounted on a support to form a unit of 46 cm² area of thickness of about 80 microns.

The membrane assembly is immersed in a 10 w % aqueous solution of lithium chloride for 24 hours at 25° C.—allowing both sides of the membrane to be treated. The assembly is then washed with water and then allowed to equilibrate in the feed stream for 24 hours.

The membrane assembly is then used to treat the charge solution by pervaporation at 25° C. The charge solution is admitted to the pervaporation cell at a rate of 0.25 gallons per minute per square foot of membrane surface. The inlet pressure on the membrane is atmospheric; and the outlet pressure is 1 mm Hg.

The retentate is a solution containing only 95 w % ethylene glycol and 5 w % water. The permeate condensed and recovered in liquid phase at 1 mm Hg is a solution containing 11.3 w % ethylene glycol and 88.7 w % water.

This corresponds to a Separation Factor of 44.5 and a Flux of 0.12 gallons per square foot per day (gfd).

EXAMPLES II-X

In this series of examples which is intended to show the effect of various counter ions, the membrane employed is the same membrane as employed in Example I. In each of Examples II-VII, the membrane assembly is treated with a different metal chloride, in the same concentration as noted in Example I followed by the same washing and equilibration.

Control Example VIII* utilizes the commercially available (from Dupont) Nafion 117 brand of perfluorinated resin of a thickness of 190 microns.

Control Example IX* utilizes the commercially available RC-100 brand of composite polyamide resin which is marketed by UOP.

Each of these membrane assemblies is employed in a manner similar to that of Example I to separate water from ethylene glycol solution. The permeate (percent of ethylene glycol in the Permeate), the Separation Factor, (Sep) and the Flux (gfd) are noted.

TABLE

| Example | Membrane | Permeate | Sep | Flux |
|---|---|---|---|---|
| II | SPE-H | 13.7 | 35.7 | 0.13 |
| III | SPE-Li | 11.3 | 44.5 | 0.1 |
| IV | SPE-Na | 11.2 | 44.9 | 0.12 |
| V | SPE-K | 11.9 | 42.0 | 0.1 |
| VI | SPE-Rb | 11.8 | 42.4 | 0.1 |
| VII | SPE-Cs | 15.0 | 32.1 | 0.09 |
| VIII* | Nafion-H 117 | 48.6 | 6.0 | 0.3 |
| IX* | RC-100 | 41.1 | 8.1 | 0.02 |

From the above table, it is apparent that the process of this invention as carried out in Examples II-VII permits attainment of high Separation Factors—above 30 at reasonable flux (e.g. 0.1). Control Examples VIII* and IX* show low Separation Factor.

EXAMPLES X-XVIII*

In this series of examples, the membrane employed in Examples X, XI, and XII is the same sulfonated polyethylene as was employed in Example I using as counter ions $Na^+$, $Cr^{+++}$, and $Cu^{++}$ derived respectively from 10 w % aqueous solutions of the corresponding chloride. In Examples XIII-XVI, the membranes are prepared from the Nafion 117 membrane by contact with 10 w % aqueous solutions of the chlorides of Na, K, Rb, and Cs respectively. Examples XVII* and XVIII* utilize the same resins as were used in Examples VIII* and IX*. Pervaporation is carried out at 75° C.

The charge capacity of the SPE is 1.66 meq/g, of the Nafion is 0.88 meq/g.

TABLE

| Example | Membrane | Permeate | Sep | Flux |
|---|---|---|---|---|
| X | SPE-Na | 31.8 | 12.2 | 0.28 |
| XI | SPE-$Cr^{+3}$ | 10.6 | 47.8 | 0.02 |
| XII | SPE-$Cu^{+2}$ | 1 | 561 | 0.002 |
| XIII | Nafion-Na | 55.7 | 4.5 | 0.17 |
| XIV | Nafion-K | 38.0 | 9.2 | 0.04 |
| XV | Nafion-Rb | 16.8 | 28.1 | 0.03 |
| XVI | Nafion-Cs | 1 | 561 | 0.01 |
| XVII* | Nafion-H 117 | 48.6 | 6.0 | 0.3 |
| XVIII* | RC-100 | 41.1 | 8.1 | 0.02 |

From the above Table, it is apparent that the process of this invention (Examples X-XVI) generally permit satisfactory operation to yield permeate of decreased content of ethylene glycol.

It will be noted that for a given membrane the Separation Factor is lower at 75° C. than at 25° C. For example, Example IV at 25° C. give much better Separation Factor at 25° C. than is obtained with Example X at 75° C. although the Flux is better at the higher temperature. Although generally the Separation Factor is the more important criterion, Flux must be considered in designing a commercial unit.

The systems of Examples XI and XII show desirably high Separation Factor although the Flux is low. Example XIII shows relatively high Flux.

EXAMPLES XX-XXXV

In this series of Examples, the general procedure of Example I is followed except that the counter ion is provided by a 10 w % solution in isopropanol of a tetraalkyl ammonium bromide (rather than sodium chloride). Pervaporation is at 75° C.

TABLE

| Example | Membrane | Permeate | Sep | Flux |
|---|---|---|---|---|
| XIX | SPE-N(Ethyl)$_4$ | 37.1 | 9.6 | 0.22 |
| XX | SPE-N(Propyl)$_4$ | 33.9 | 11.0 | 0.44 |
| XXI | SPE-N(Butyl)$_4$ | 29.2 | 13.7 | 0.31 |
| XXII | Nafion-N(Methyl)$_4$ | 39.2 | 8.8 | 0.12 |
| XXIII | Nafion-N(Butyl)$_4$ | 23.7 | 18.2 | 0.05 |
| XXIV* | Nafion-H 117 | 48.6 | 6.0 | 0.3 |
| XXV* | RC-100 | 41.1 | 8.1 | 0.02 |

From the above Table, it is apparent that as the R group in the $R_4NX$ agent is increased in chain length from 2 to 4, the Separation Factor increases from 9.6 to 13.7. The Flux is desirably high throughout the range, peaking at 0.44 (the highest Flux recorded) for the n-propyl quaternary ammonium. Comparison of Examples XXII-XXIII shows superiority of the butyl quaternary ammunium counter ion over the methyl with respect to Separation Factor.

EXAMPLES XXVI-XXXI

In this series of Examples, the general procedure of Examples XIX-XXV* is followed except that the charge solution contains 90 w % isopropanol in water.

TABLE

| Example | Membrane | Permeate | Sep | Flux |
|---|---|---|---|---|
| XXVI | SPE-Li | 2.7 | 324 | 0.1 |
| XXVII | SPE-Rb | 1.1 | 809 | 0.09 |
| XXVIII | SPE-Cr | 3.4 | 256 | 0.04 |
| XXIX | Nafion-Li | 55.9 | 7.1 | 0.2 |
| XXX | Nafion-Cs | 16.1 | 46.9 | 0.03 |
| XXXI | Nafion-Cr | 42.2 | 12.3 | 0.1 |

From the above Table it is apparent that higher Separation Factors are attained with the sulfonated polyethylene.

EXAMPLES XXXII-XXXIII

In this series of Examples, the general procedure of Examples XXVI-XXXI is followed. The charge solution is 90 w % isopropanol-water at 70° C. The counter ions are organic.

TABLE

| Example | Membrane | Permeate | Sep | Flux |
|---|---|---|---|---|
| XXXII | SPE-N(Butyl)$_4$ | 88.0 | 1.2 | 0.82 |
| XXXIII | SPE-N(Octyl)$_4$ | 64.6 | 4.9 | 0.18 |

Although this invention has been illustrated by reference to specific embodiments, it will be apparent to those skilled in the art that various changes and modifications may be made which clearly fall within the scope of the invention.

We claim:

1. The method which comprises
    passing a charge aqueous solution of ethylene glycol into contact at 40° C.-120° C. with, as a pervaporation membrane, (i) a perfluorinated resin membrane having the formula

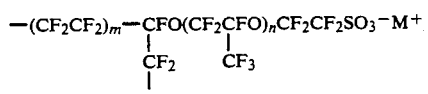

wherein M is a metal, m is a number indicating the number of $(CF_2CF_2)$ groups, and n is a number indicating the number of

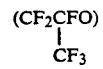

groups, said resin membrane bearing, as a counter ion, a metal of Groups IA, IB, IV B, V B, VI B, or VIII of the Periodic Table or a quaternary ammonium group $R_4N$ wherein R is a lower alkyl, and each R group contains less than 6 carbon atoms;
    maintaining a pressure drop across said pervaporation membrane thereby forming (i) a retentate containing an increased concentration of ethylene glycol and a decreased content of water and (ii) a permeate containing a decreased concentration of ethylene glycol and an increased concentration of water;
    recovering said retentate containing increased concentration of ethylene glycol and decreased concentration of water; and
    recovering said permeate containing increased concentration of water and decreased concentration of ethylene glycol.

* * * * *